United States Patent [19]

Funk et al.

[11] Patent Number: 4,534,229
[45] Date of Patent: Aug. 13, 1985

[54] METHOD AND APPARATUS FOR PREPARING A MEAT SAMPLE FOR DETERMINATION OF COMPOSITION OF SAME

[75] Inventors: David B. Funk, Auburn; James B. Kallmeyer, Glenarm, both of Ill.

[73] Assignee: Dickey-john Corporation, Auburn, Ill.

[21] Appl. No.: 478,254

[22] Filed: Mar. 24, 1983

Related U.S. Application Data

[63] Continuation-in-part of Ser. No. 375,552, May 6, 1982, Pat. No. 4,496,907.

[51] Int. Cl.³ .............. G01N 1/28; G01N 1/08; G01N 25/00; G01N 33/12
[52] U.S. Cl. ................... 73/863; 73/432 R; 73/864.44; 374/45; 374/157; 426/231
[58] Field of Search ............. 73/863, 432, 864.44, 73/864.45, 432 R; 374/45, 157; 426/231

[56] References Cited

U.S. PATENT DOCUMENTS

| | | | |
|---|---|---|---|
| 473,316 | 4/1892 | Hunter | 73/864.45 |
| 2,331,227 | 10/1943 | Proudlock | 374/157 |
| 3,273,930 | 9/1966 | Gottfried | 73/864.44 X |
| 3,282,115 | 11/1966 | Taylor et al. | 73/432 Z |
| 3,444,938 | 5/1969 | Ballmonn | 73/864.44 X |
| 3,557,625 | 1/1971 | Leger, Jr. et al. | 73/432 Z |
| 3,734,741 | 5/1973 | Larsen | 426/231 |
| 4,496,907 | 1/1985 | Funk | 324/445 |

FOREIGN PATENT DOCUMENTS

| | | | |
|---|---|---|---|
| 2608651 | 9/1977 | Fed. Rep. of Germany | 73/432 Z |
| 62476 | 9/1969 | German Democratic Rep. | 73/864.45 |
| 8103547 | 12/1981 | PCT Int'l. Appl. | 426/231 |

Primary Examiner—Stewart J. Levy
Assistant Examiner—Tom Noland
Attorney, Agent, or Firm—Trexler, Bushnell & Wolters, Ltd.

[57] ABSTRACT

A novel method for preparing a ground-meat sample for compositional analysis and an apparatus for performing the method are disclosed. The method comprises a series of steps. The first step includes obtaining a predetermined quantity of ground meat. Next, the meat is formed into a layer having a predetermined thickness. Then, a first portion of the layer is isolated from the remainder. The isolated first portion is then urged into an elongated, hollow member having an axis, an open end, and a resistive end movable along the axis relative to the open end. The isolated first portion and the resistive end are then urged together so as to produce a substantially air void-free isolate out of the first portion. Next, a subsequent portion of the layer is isolated from the remainder and urged into the hollow member and against the isolate already in the hollow member thereby adding to the isolate already in the hollow member and causing the resistive end and the isolate engaging the resistive end to move axially through the hollow member. Lastly, the hollow member is repeatedly filled with subsequent portions, in the manner described immediately above, until and hollow member is predeterminedly filled with the ground meat thereby producing an analyzable meat sample. The apparatus for loading the ground-meat sample into the elongated hollow member comprises closure and packing members. The closure member defines the axially-movable resistive end.

22 Claims, 14 Drawing Figures

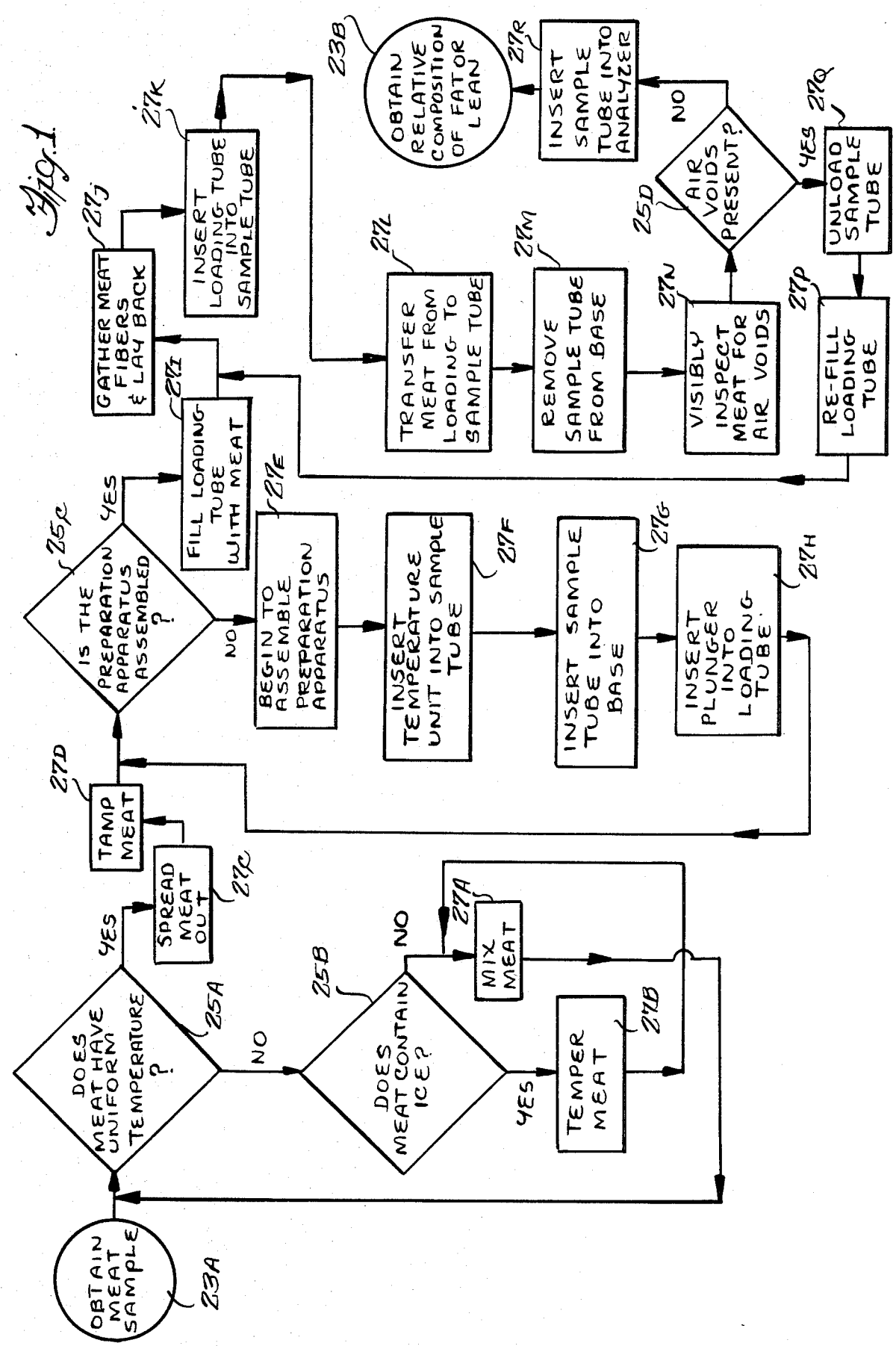

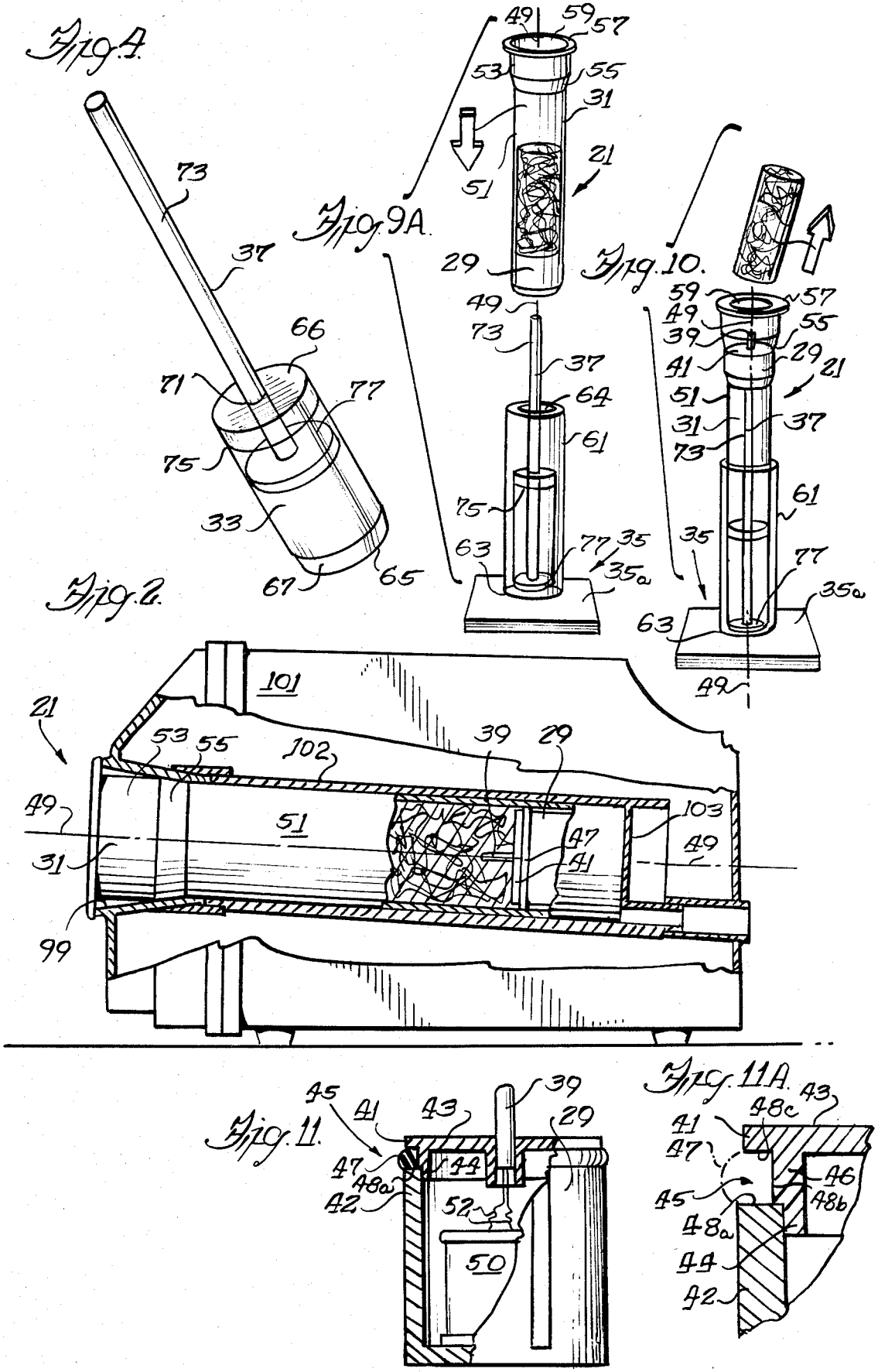

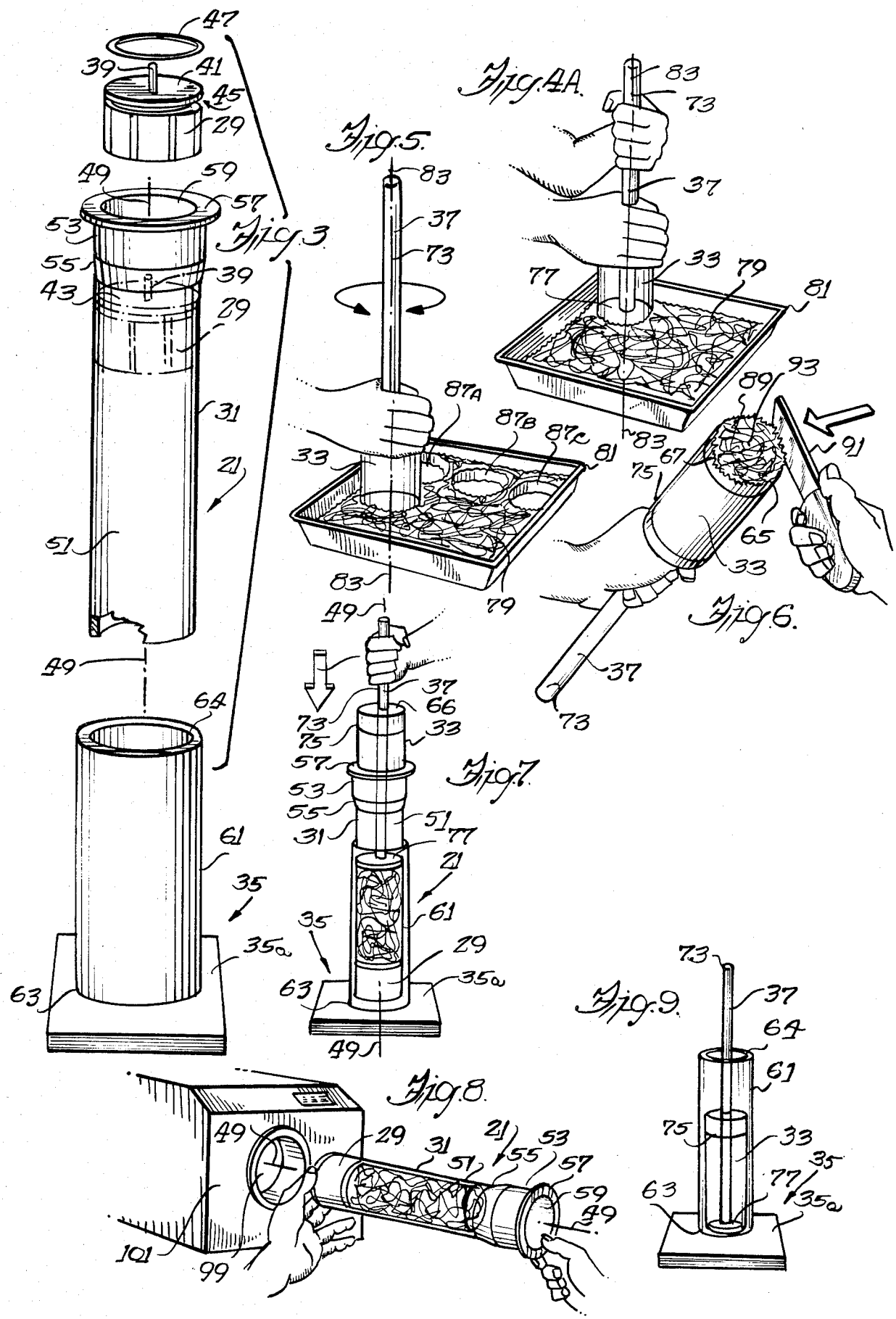

METHOD AND APPARATUS FOR PREPARING A MEAT SAMPLE FOR DETERMINATION OF COMPOSITION OF SAME

REFERENCE TO RELATED APPLICATION

The instant application is related to and is a continuation in part of the application entitled "Method and Apparatus for Non-Destructively Determining Ingredients of a Sample" (bearing Attorney-Docket No. Case 81, 180/23162), filed May 6, 1982 and assigned Ser. No. 375,552, and now U.S. Pat. No. 4,496,907 is herein incorporated by reference for purposes of 35 U.S.C. Section 120.

The instant and related applications have both been assigned to Dickey-john Corporation, a Delaware corporation, which has its principal place of business at Auburn, Ill.

BACKGROUND OF THE INVENTION

The present invention relates to non-destructive determination of composition of a meat sample, preferably a freshly-ground meat sample. More particularly, the present invention is directed to a method and an apparatus for preparing such a meat sample for composition determination.

In light of recent advances in technology, a wide variety of testing or analyzing devices (non-destructive in relation to the sample being tested) are becoming increasingly commercially available. Some of these devices (or apparatuses) require preparation of the sample prior to analyzing or testing.

The above-referenced related application, for example, describes an apparatus which non-destructively determines the relative percentage of fat or lean in a ground-meat sample.

The instant application further discloses such analyzing apparatus and describes a novel method and apparatus for preparing such a ground-meat sample for relative fat- or lean-content analysis.

Non-destructive sample-analyzing or -testing devices or apparatuses are additionally becoming increasingly economically popular because of the substantial reduction of time required to obtain desired sample information, as compared to traditional destructive-testing or -analyzing laboratory practices. However, problems may be encountered in cleaning and sterilizing such apparatuses, particularly when used for testing meats and the like, such meats subsequently being used for human consumption.

OBJECTS AND SUMMARY OF THE INVENTION

Accordingly, it is a general object of this invention to provide a novel apparatus for analyzing products such as ground meat and the like and for preparing a ground-meat sample for non-destructive analysis (the analysis being directed preferably to relative composition of fat or lean in the sample).

A related object is to provide a method for the assembly of such a preparative apparatus.

Yet another object is to provide a method for preparing the meat sample for analysis using the apparatus of the instant invention.

Briefly, and in accordance with one aspect of the present invention, a novel method for preparing a ground-meat sample for compositional analysis, will now be summarized. The method comprises a series of steps. The first step includes obtaining a predetermined quantity of ground meat. The meat has a predetermined particle size. Next, the meat is formed into a layer having a predetermined thickness. Then, a first portion of the layer is isolated from the remainder. The isolated first portion is then urged into an elongated hollow member having an axis, an open end, and a resistive end movable along the axis relative to the open end. The isolated first portion and the resistive end are then urged together so as to produce a substantially air void-free isolate out of the first portion. Next, a subsequent portion of the layer is isolated from the remainder and urged into the hollow member and against the isolate already in the hollow member thereby adding to the isolate already in the hollow member and causing the resistive end and the isolate engaging the resistive end to move axially through the hollow member. Lastly, the hollow member is repeatedly filled with additional subsequent portions, in the manner described immediately above, until the hollow member is predeterminedly filled with the ground meat thereby producing an analyzable meat sample.

In accordance with yet another aspect of the present invention, an apparatus for performing this method will also now be summarized. The apparatus for loading the ground-meat sample into the elongated hollow member comprises closure means and packing means. The closure means defines the axially-movable resistive end. The packing means is for axially urging the meat into the hollow member so as axially to move the closure means for preventing substantially the formation of air voids in relation to the ground-meat sample being packed into the hollow member.

BRIEF DESCRIPTION OF THE DRAWINGS

The foregoing, as well as other objects, features or advantages of the present invention will become more readily understood upon reading the following detailed description of the illustrated embodiments, together with reference to the drawings, wherein:

FIG. 1 is a logic diagram of a preferred method of preparing a meat sample for analysis, in accordance with the present invention;

FIG. 2 is a side view, partially in section, of a loaded sample tube of the instant invention inserted into a composition analyzer;

FIG. 3 is an exploded isometric view, illustrating partial assembly of a sample preparation apparatus of the instant invention;

FIG. 4 is an isometric view of an assembled plunger and loading tube of the sample preparation apparatus;

FIG. 4A is an isometric presentation of a preferred method of manually cooperatively using the plunger and loading tube to obtain a spread-out ground-meat sample;

FIG. 5 is an isometric presentation of a preferred method of manually filling the loading tube;

FIG. 6 is an isometric presentation of a preferred method of manually gathering loose ground-meat fibers which extend beyond the opening of a filled loading tube;

FIG. 7 is an isometric presentation of a preferred method of manually transferring the ground-meat sample from the loading tube into the sample tube;

FIG. 8 is an isometric presentation of a preferred method of inserting a meat-filled sample tube into the meat composition analyzer (referred to above);

FIG. 9 is an isometric presentation of a preferred method of inserting the loading tube and plunger into a tubular member of a loading base for the purpose of preparing to unload the meat sample from the meat-filled sample tube;

FIG. 9A is an isometric presentation of a preferred method of cooperatively using the plunger, loading tube and loading base to urge the meat sample out of the meat-filled sample tube;

FIG. 10 is an isometric presentation of a result of practicing the method presented in FIG. 9A, the meat sample having been unloaded from the sample tube by axially urging the sample tube toward the base and using the plunger handle to unload the meat sample;

FIG. 11 is a side view, partially in section, of a preferred embodiment of the temperature-determining unit, in accordance with the present invention; and FIG. 11A is a detailed view, in enlarged scale in relation to FIG. 11, illustrating cover-closure detail of the temperature-determining unit disclosed in FIG. 11.

DETAILED DESCRIPTION OF THE ILLUSTRATED EMBODIMENTS

THE ANALYSIS METHOD AND APPARATUS

FIG. 1 is a block diagram presenting a process for meat-sample preparation, utilizing an apparatus 21 in accordance with the instant invention. The circles 23A, 23B represent termini, i.e., starting and ending points. The diamonds 25A, 25B, 25C and 25D represent decision-requiring points where a "yes" or "no" answer is required. The rectangular boxes 27A, 27B, 27C, 27D, 27E, 27F, 27G, 27H, 27I, 27J, 27K, 27L, 27M, 27N, 27P, 27Q and 27R represent transfer functions; i.e., these boxes describe what is transpiring along a particular branch of the decision-making flow path.

Separate steps or portions of FIG. 1 are discussed below under appropriately-captioned headings.

In FIG. 2, the apparatus 21 is shown as including an analyzer or tester 101. For a detailed description of the structure and functioning of the tester 101, reference is made to the above-identified co-pending application. It suffices to state here that the tester 101 includes a sample receiving tube 31 (described below) insertable into a housing 102 for testing. The tester 101 includes electromagnetic coil means and circuitry for providing a magnetic field around the housing 102 and for sensing the effect on the field (provided by the insertion of a sample to be tested) and ultimately for emitting a read out or other indication of the constituents of the sample.

The apparatus 21 of the instant invention further comprises a temperature-determining unit 29 (FIG. 11), insertable into the sample tube 31 (FIG. 3).

A loading tube 33 (FIG. 4), a loading base 35 (FIG. 3), and a plunger 37 (FIG. 4) are provided for loading the sample tube 31 (as described below).

The temperature-determining unit 29, which preferably is substantially cylindrical, includes a temperature probe 39. The temperature probe 39 is substantially centrally located in an end cap 41. The cap 41 snugly fits into a cylindrical shell 42 of the unit 29 (FIGS. 11, 11A).

Referring to FIG. 11A, it will be seen that the end cap 41 has a top surface 43. The end cap 41 includes a first annular shoulder 46 which is integral with and which depends downwardly from the end cap 41. Integral with and depending downwardly from the first shoulder 46 is a second shoulder 44. The second shoulder 44 is circumferentially engageable along the outer surface thereof with the upper inner periphery of the cylindrical shell 42. Intermediate the top surface 43, the first shoulder 46, and the cylindrical shell 42, is a generally horizontal, upper-end surface 48a of the cylindrical shell 42, a generally vertical, external surface 48b of the first shoulder 46, and a generally horizontal, underside surface 48c of the end cap 41, all of which surfaces 48a, 48b and 48c define a circumferential slot or groove 45 intermediate the end cap 41 and the shell 42. An elastomeric O-ring 47 (FIGS. 3, 11 and 11A) of appropriate size is seatable in the groove 45. Within the unit 29, the probe 39 is connected via wires 52 to a suitable, commercially available, current-to-frequency converter 50.

Prior to being seated in the groove 45, the O-ring 47 is lubricated with a commercially available lubricant. Preferred lubricants are vegetable shortening, lard, or any one of a variety of commercially available lubricants which have been approved by FDA/USDA for use on meat-handling equipment.

Referring to FIG. 2, it will be seen that the sample tube 31 is preferably elongated and substantially hollow. The preferred sample tube 31 is an elongated tubular member (FIGS. 3, 7, 8, 9A and 10). About an axis 49 of the sample tube 31, is included a sample analyzer-negotiating section 51 (FIG. 2), a temperature unit-receiving section 53 (FIG. 3), and a tapered portion 55 which is intermediate and integral with these two sections 51, 53. The unit-receiving section 53 preferably is relatively greater in diameter about the axis 49 than the analyzer-negotiating section 51. The inner diameter of the tapered portion 55 preferably uniformly decreases along the axis 49, from the unit-receiving section 53 to the analyzer-negotiating section 51, thereby providing the tapered portion 55 with an inner surface generally describing an annular portion of a conical section.

The unit-receiving section 53 has an annular lip 57 (FIG. 3) which extends radially outwardly from an inlet 59 of the sample tube 31. The temperature-determining unit 29 is readily insertable (via the inlet 59) into the sample tube 31, through the unit receiving section 53 and tapered portion 55, and into the uppermost portion of the analyzer-negotiating section 51 (the uppermost portion herein being defined as the boundary of the tapered portion 55 and the analyzer-negotiating section 51) where the O-ring 47, snugly engageable with the inner periphery of the analyzer-negotiating section 51 when seated in the slot 45, prevents further downward movement of the unit 29 into the analyzer-negotiating section 51. Additional force, having a component applied generally along the axis 49, is required to urge the unit 29 into the analyzer-negotiating section 51 (FIG. 3). The inner diameter (see FIG. 2) of the analyzer-negotiating section 51, otherwise, is relatively greater in dimension about the axis 49 than the outer periphery of the temperature-determining unit 29.

It is to be noted that as the unit 29 is pushed through the tube 31, the O-ring 47 wipes clean the internal surface of the sample tube 31 and thereby substantially prevents contamination to a sample (being tested) by any residue from a previous sample. Furthermore, whenever desired, the unit 29 can be completely removed so that both it and the tube 31 can be easily washed and sterilized.

The external end of the analyzer-negotiating section 51 is flush (FIG. 3), and through such end the temperature-determining unit 29 is slidably movable.

PREPARATION APPARATUS

The loading base 35 (FIG. 3) includes a flat, rigid base or platform 35a, which supports a preferably elongated, substantially hollow member 61. The hollow member 61 is preferably tubular, and preferably has an inner periphery (detail not shown) which is slidably engageable with the outer periphery of the analyzer-negotiating section 51 of the sample tube 31. One end 63 of the tubular member 61 is preferably fixed to the base 35a and preferably extends perpendicularly therefrom. The other end 64 of the tubular member 61 is open.

The loading tube 33 (FIG. 4) preferably is elongated and substantially hollow. The loading tube 33, more preferably, is tubular. One end 65 of the loading tube 33 is open; the other end 66 defines an integral end closure. The loading tube 33 has an outer periphery which is slidably circumferentially engageable with the inner periphery of the temperature unit-receiving section 53 of the sample tube 31 (FIG. 7). The open end 65 of the loading tube 33 includes an external, peripheral-edge surface, preferably presenting a conical section 67, the outer periphery of which meshes substantially with the inner periphery (see FIG. 7) of the tapered portion 55 of the sample tube 31. The other end 66 of the loading tube 33 includes a relatively small-diameter (in relation to the loading-tube diameter), substantially centrally-located, through bore or aperture 71 through which a cylindrical handle 73 of the plunger 37 is slidably insertable. The loading tube 33 has a scribe line 75 (FIG. 4) which is circumferentially carried by the loading tube 33 and which is located proximate to the substantially closed-off end 66 of the loading tube 33.

In addition to the handle 73, the plunger 37 includes a disc 77 (FIG. 4) which is preferably affixed at one end of the plunger handle 73. The affixed handle 73 is preferably centrally located upon one surface of the disc 77 and extends preferably perpendicularly therefrom. The disc 77 is preferably cylindrical. The circumferential edge of the disc 77 is such that the disc 77 is axially slidable through the loading tube 33 and axially, snugly slidable through the sample analyzer-negotiating section 51 of the sample tube 31 (FIG. 7). The handle 73 has a length sufficient for transferral of a ground-meat sample from the loading tube 33 into the sample tube 31 (see FIG. 7).

The following describes how the above-described apparatus is used to prepare a ground-meat sample for analysis.

ESTABLISHING UNIFORM TEMPERATURE THROUGHOUT SAMPLE

The effective product-grind diameter of a ground-meat sample (FIG. 1: 23A) to be analyzed for relative fat or lean content is preferably 3/8 of an inch (about 0.953 centimeters) or less. Effective product-grind diameter refers to the diameter of a die (die not shown) through which the meat sample has been urged. It is preferable to use freshly-ground meat to avoid moisture losses (due to evaporation) which might otherwise occur prior to analysis. Sample analysis therefore is performed preferably within one hour of grinding.

The ground-meat sample to be analyzed is next manually or otherwise worked to assure that it has a substantially uniform temperature profile throughout (FIG. 1: 25A). If it does not, the sample must next be mixed or combined (FIG. 1: 27A) until a substantially uniform temperature profile is established. If, in addition, it is apparent that the sample contains ice crystals (FIG. 1: 25B), it is suggested that at least one of the following five alternative methods (presented below) of tempering the sample (FIG. 1: 27B) be employed prior to mixing or combining (to establish the uniform temperature profile, as mentioned above).

Samples which contain crystals of ice should preferably be tempered to eliminate substantially all ice prior to sample analysis. The presence of ice in the sample may result in the generation of false or otherwise inaccurate compositional information about the sample.

One method of investigating the presence of ice crystals, for example, is by pulling the ground meat apart and, in the presence of light, noting areas in the meat where light is reflected.

Use of the first tempering method listed hereinbelow is suggested when relatively minimal amounts of ice crystals are present. Tempering methods 3, 4 and/or 5 may be employed where the sample contains a substantial amount of ice. Tempering methods 2, 3 and/or 4 may be employed when the sample contains an amount of ice which is intermediate these two extremes.

During tempering, loss of meat moisture and/or cooking of the meat preferably should be avoided. The object of tempering preferably is uniformly to raise the temperature of the sample a sufficient amount to melt the ice.

After tempering, the sample preferably is then mixed. The purpose of mixing the sample (preferably by hand), is substantially to eliminate localized areas or regions of relatively-elevated temperature (so-called hot spots) within the sample.

During tempering, it is preferable to avoid overworking the ground-meat sample. Overworking is discussed below in point No. 2 of the PRE-LOADING PROCEDURE.

TEMPERING METHODS

1. When ice is not present, the sample need not be tempered (see FIG. 1: 25B, 27A, 27B). When it appears that there are minimal amounts of ice crystals present, it is preferable to thoroughly work (i.e., mix or combine portions of) the sample, preferably by hand, such as for about 5 minutes.

2. For situations where more than minimal amounts of ice are present in the sample, it is suggested, first, that the sample be spread out preferably in a relatively large, flat pan (FIG. 4A). Upon being spread out, the sample ought to have, it is suggested, a thickness which preferably ranges from about ¾ inches to about 1 inch (about 1.91 centimeters to about 2.54 centimeters). Next, it is preferable that the sample be set aside at room temperature, defined in this application to be a temperature range of from about 65 degrees Fahrenheit to about 75 degrees Fahrenheit (from about 18.3 degrees Centigrade to about 23.9 degrees Centigrade), for at least ½ of an hour. Then, it is suggested that the sample be mixed (see FIG. 1: 27A) or combined, preferably by hand, to obtain a substantially uniform temperature profile throughout the sample.

3. Another method for melting the ice contemplates use of a warm water bath. This method comprises first placing the sample in a plastic bag of sufficient strength and appropriate size for effectively containing the sample without rupturing of the bag. This method includes then sealing or otherwise closing the bag so as substantially to isolate the sample from the water (of the warm-water bath, into which the bag and sample is to be immersed). This method further includes immersing the bag in the bath for an amount of time sufficient to melt substantially all the ice in the sample. Then, as soon as it has been determined that a substantial amount of the ice has been melted, it is suggested that the last step of this method include mixing of the sample, preferably by hand, to obtain a uniform temperature profile throughout the sample.

4. A fourth suggested method for melting the ice contemplates, first, spreading the sample out (if it is possible to do so). The fourth method next includes the step of placing the sample in a microwave oven, and operating the oven in a manner sufficient to cause the sample to thaw.

Most commercially available microwave ovens generally will cause the sample to be relatively hotter at the center than at the surface of the sample. It is suggested that cooking or overheating of the sample be avoided. It is further suggested therefore that appropriate microwave-oven operating procedures be used to cause the sample to thaw without causing cooking or overheating of the sample. Depending upon the kind or model of microwave oven employed, it may be desirable to subject the sample to several microwave-oven heating cycles and to inspect the sample for hot spots after each heating cycle.

Once the sample has thawed, it is suggested that the sample be mixed, preferably by hand, to obtain a uniform temperature profile throughout.

5. A fifth suggested method for melting the ice contemplates re-grinding the sample. The temperature of the grinder is preferably maintained at about 31 degrees Fahrenheit (−0.6 degrees Centigrade) or slightly greater than this temperature during re-grinding; and the effective product re-grind diameter is preferably about ⅛ inches (0.318 centimeters), which is a relatively smaller diameter than discussed above in relation to the sample as originally obtained (FIG. 1: 23A) for analysis.

It may be desirable to re-grind the sample more than once.

As soon as it has been established that a substantially uniform temperature exists throughout the sample, it is suggested that the sample be prepared for loading into the sample tube 31. A preferred method for preparing the sample for loading is presented below. Prior to loading the sample into the sample tube, however, it is suggested that a preferred preloading method be performed upon the sample. The preferred pre-loading method is also presented below.

It is further suggested that the preparation apparatus be assembled (FIG. 1: 25C) prior to performing the pre-loading method. A preferred method for assembling the preparation apparatus is presented hereinbelow.

ASSEMBLY OF PREPARATION APPARATUS

1. It is suggested that the first step (FIG. 1: 27E) in assembling the preparation apparatus include lubricating the O-ring 47 (FIG. 3).

2. It is further suggested that the O-ring 47 next be installed on the temperature-determining unit 29 by seating the O-ring 47 in the groove 45 (FIG. 11).

3. It is next suggested that the temperature-determining unit 29 be inserted (FIG. 1: 27F) into the sample tube 31 (FIG. 3) so that the temperature probe 39 is disposed outwardly through the opening 59 of the temperature unit-receiving section 53.

With the O-ring 47 seated in the groove 45, the temperature-determining unit 29 preferably snugly engages the inner periphery of the analyzer-negotiating section 51.

It is further suggested that the temperature-determining unit 29 be seated in the sample tube 31 so that the end surface 43 (please refer to FIG. 11), from which the temperature probe 39 extends, preferably is lined up proximate to the reduced end of the tapered portion 55 of the sample tube 31 (please refer to FIG. 3).

4. It is next suggested that the analyzer-negotiating section 51 of the sample tube 31 be inserted (FIG. 1; 27G) into the tubular member 61 of the loading base 35 (FIG. 3).

5. It is further suggested that the free end of the handle 73 of the plunger 37 next be inserted (FIG. 1: 27H) into the open end 65 of the loading tube 33, and that the handle 73 next be axially extended through the aperture 71 of the end closure 66 so as to draw the disc 77 axially into the loading tube 33 (FIG. 4).

PRE-LOADING PROCEDURE

1. Prior to the sample being loaded into the preparation apparatus, it is suggested, as a first step of the pre-loading method, that the ground-meat sample first be spread out relatively evenly (FIG. 4A; FIG. 1: 27C). This preferably is done by manually employing the loading tube 33 and the plunger 37 to spread out a preselected ground-meat sample 79. More particularly, by referring to FIG. 4A, it will be seen that the disc 77 preferably is manually used to urge the sample 79 into uniform thickness. The meat sample 79 is spread out in such a manner, preferably to a thickness ranging from about 1 inch to about 1½ inches (about 2.5 centimeters to about 3.8 centimeters).

A commercially available, nominal 8 inch by 8 inch by 2 inch (20.3 centimeters by 20.3 centimeters by 5.1 centimeters) deep baking pan 81, for example, provides a suitable container for spreading a 2½-pound to about 3-pound (1.1-kilogram to about 1.4-kilogram) quantity of ground-meat sample 79 to such a thickness.

2. It is suggested that a second step in the pre-loading method include gently tamping (see FIG. 1: 27D) the spread-out meat sample 79 substantially to dispel all air voids (details of such air voids are not shown), if any air voids are present in the spread-out sample 79.

During the tamping step, it is suggested that care be taken to avoid overworking the ground-meat sample. Overworking of the sample is evidenced by bleeding. Noticeable bleeding of the meat or the presence of air voids in the meat may result in the generation of false or otherwise inaccurate compositional information about the sample.

3. If the preparation apparatus is not yet assembled, the pre-loading method further contemplates assembling the preparation apparatus (FIG. 1: 25C) preferably following the steps outlined above (FIG. 1: 27E-27H). Otherwise, if the preparation apparatus has already been assembled, it is suggested that the steps for loading the preparation apparatus, which are outlined below, next be performed (FIG. 1: 27I).

PROCEDURE FOR LOADING OF PREPARATION APPARATUS

1. As a first step in loading a ground-meat sample into the preparation apparatus, it is suggested that the loading tube 33 be placed upon the surface of the manually spread-out ground-meat sample 79 in the pan 81 (the handle 73 preferably being upwardly perpendicularly disposed relative to the surface of the sample 79) and that the disc 77 (in the loading tube 33) axially next be urged into contact with the surface of the meat sample 79 (FIG. 4A).

2. Then, preferably with one hand, it is suggested that the handle 73 be grasped and that the surface of the disc 77 be urged against the surface of the meat sample 79. It is further suggested that the loading tube 33 be twisted, such as by using the other hand, about the loading tube axis 83 while, preferably at the same time, urging the loading tube 33 through the meat sample 79 (FIG. 4A). This action initially forces a disc or patty of ground-meat sample 79 into the loading tube 33 thereby partially filling the loading tube 33 and bringing the open end 65 of the loading tube 33 into engagement with the bottom of the pan 81.

Before lifting the partially-filled loading tube 33 out of the pan 81, it is next suggested that the meat sample patty in the loading tube 33 firmly be tamped, preferably using the disc 77 of the plunger 37, so that the meat sample patty becomes compressed within the loading tube 33 so as to cause the patty within the loading tube 33 to remain in the loading tube 33 after the loading tube 33 has been lifted out of the pan 81.

3. It is next suggested that the partially-filled loading tube 33 upwardly be lifted out of the meat-sample tray 81. It will be noted, by referring to FIG. 5, that a preferably substantially circular hole 87A will be seen in the pan 81 (FIG. 5) after the partially-filled loading tube 33 is lifted therefrom, if the loading tube 33 carefully has been loaded following the above-presented steps. If the patty is not entirely lifted out, it is suggested that the loading tube 33 be unloaded and that the loading procedure be re-started.

4. After the partially-filled loading tube 33 has been lifted out of the pan 81, it is next suggested that the loading tube 33 be placed, again preferably substantially perpendicularly, upon a remainder portion of the surface of the meat-sample 79 (i.e., that surface portion which does not include the hole 87A), that the partially-filled loading tube 33 be twisted, preferably about the loading tube axis 83, and that sufficient force be exerted upon the handle 73 so as to cause a subsequent patty to be urged into the loading tube 33. It is further suggested that the plunger handle 73 not be restricted or impeded as the loading tube 33 fills with such subsequent meat patty. It is yet further suggested that additional tamping not be performed.

5. It is next suggested that steps 3 and 4 (appearing immediately above) be repeated until the loading tube 33 is filled (FIG. 1: 27I) at least to the scribe line 75 (FIG. 6) with meat sample patties. It is suggested that, in addition to performing steps 1 and 2 (above) it will be necessary to perform several repetitions of steps 3 and 4 before the loading tube 33 substantially is filled to the scribe line 75. (Additional holes 87B, 87C, which subsequently are formed in the sample 79, are shown in FIG. 5.)

As a note of caution, it is suggested that the loading tube 33 not be overfilled. A variety of problems associated with overfilling of the loading tube 33 can come about when the plunger disc 77 is caused to come into contact with the inside surface of the end closure 66 of the loading tube 33 (FIG. 4). By avoiding such overfilling, for example, it is hoped that jamming engagement of the end closure 66 with the disc 77 is avoided.

6. With the loading tube 33 substantially filled with meat patties, it is suggested that the loading tube 33 next be secured (such as by manually grasping the handle 73 at the end closure 66 with one hand), and it is further suggested that all meat fibers 89 extending from the open end 65 be gathered (FIG. 1: 27J) and urged onto an end surface 93 of the meat sample in the loading tube 33.

A preferred manner of performing this step is shown in FIG. 6, wherein it is shown that with a suitable implement, such as a spatula 91, the meat fibers 89 can be urged back onto the end surface 93 of the sample. It is to be noted that air voids can occasionally form at the meat-patty-and-loading-tube interface during this step. It is suggested that the formation of air voids, particularly around the edge of the end surface 93, be avoided (for reasons outlined above in point No. 2 of the PRE-LOADING PROCEDURE).

7. It is next suggested that the meat sample end 65 (FIG. 6) of the loading tube 33 axially be inserted into the sample tube 31 (FIG. 1: 27K), and the sample tube 31 be inserted into the tubular member 61 so that the bottom end of the analyzer-negotiating section 51 engages the base 35 at the lower end 63 of the tubular member 61. From such an initial position, it is further suggested that the meat sample (in the loading tube 33) and the temperature-determining unit 29 (in the sample tube 31, please refer to FIG. 3) together downwardly be urged through the sample tube 31 and through the tubular member 61 toward the base 35. The result of such action is to transfer (FIG. 1: 27L) the meat sample from the loading tube 33 into the sample tube 31. Such action also preferably results in the seating of the temperature-determining unit 29 into the bottom of the sample tube 31, with the temperature-determining unit 29 preferably engaging the base 35 (FIG. 7).

8. After the sample has been transferred from the loading tube 33 into the sample tube 31, the loading tube 33 is removed from the sample tube 31. As an example, it is suggested that the plunger handle 73 be grasped and upwardly pulled so as to remove the loading tube 33 from the sample tube 31 (FIG. 7). If disengagement of the loading tube 33 from the sample tube 31 poses a problem, it is further suggested that the loading tube 33 be twisted about the sample tube axis 49, such as, for example, by using one hand to secure the sample tube 31 while using the other hand to rotate the loading tube 33 about the axis 49 relative to the sample tube 31, and to lift the loading tube 33 out of the sample tube 31.

9. To remove the meat-filled sample tube 31 from the tubular member 61 of the base 35 (FIG. 1: 27M), it is next suggested that the lip 57 of the sample tube 31 be grasped, and that the sample tube 31 axially be removed from the tubular member 61. If disengagement of the sample tube 31 from the tubular member 61 poses a problem, it is further suggested that the sample tube 31 be twisted about the sample tube axis 49 (relative to the tubular member 61) while axially removing the sample-filled sample tube 31 from the tubular member 61.

10. It is next suggested that the meat in the sample tube 31 be inspected (FIG. 1: 27N), preferably visually, so as to look for the presence of significant air voids.

11. If significant air voids are present (FIG. 1: 25D), it is next suggested that the meat in the sample tube 31 be unloaded (FIG. 1: 27Q) therefrom (preferably following the procedure for unloading the sample tube 31, outlined below). If the sample has to be unloaded, it may be necessary to obtain and prepare (FIG. 1: 27P) a new meat sample so that analysis of the ground-meat sample can be performed. To re-load the sample tube 31, it is suggested that the step for loading the tube 33 with meat, and the subsequent steps (outlined above) be followed. Prior to re-loading, it may be necessary to wipe or otherwise remove all meat and fat from the surface of the sample tube 31.

Since overworking of the meat may result in the generation of erroneous meat-composition information, re-use of the unloaded meat is not suggested. Rather, with a new meat sample, it is suggested, for example, that steps 1-10 (outlined immediately above) be followed to obtain a sample containing substantially no air voids. It may occasionally be necessary to start with a fresh meat sample, following the pre-loading procedure outlined above.

12. Otherwise, with substantially no air voids present in the meat in the sample tube 31, it is suggested that the sample analyzer-negotiating section 51 (of the meat-filled sample tube 31) next be inserted (FIG. 1: 27R) into an appropriate sample tube-receiving port 99 of the sample analyzer 101 (FIG. 8) for obtaining relative composition of fat or lean (FIG. 1: 23B). It will be noted, by referring to FIG. 2, that the analyzer 101 preferably includes a base 103 at the inner end of the housing 102 for locating the sample tube 31 inserted through the port 99.

When inserting the (sample filled) analyzer-negotiating section 51 into the tube-receiving port 99, it is suggested that the sample tube 31 be handled substantially as presented in FIG. 8 to minimize transfer of body heat to the meat sample therein.

13. When using the sample analyzer 101 described in the above-referenced pending application, the sample tube 31 is preferably seated against the base 103 (FIG. 2) of the tube-receiving port 99.

UNLOADING OF SAMPLE TUBE

1. To unload the meat from the sample tube 31, it is suggested that the plunger 37 be placed in the loading tube 33 (FIG. 4) and that the loading tube 33 be inserted into the tubular member 61 in a manner such that the plunger handle 73 protrudes outwardly from the tubular member 61, and the plunger disc 77 contacts the loading base 35 (FIG. 9).

2. It is next suggested that the temperature-determining unit 29 (in the sample tube 31) be urged into engagement with the end of the plunger handle 73 (FIG. 9A).

3. It is further suggested that the sample tube 31 be grasped and urged toward the base 35, thereby causing the meat sample to be displaced from the sample tube 31 (FIG. 10).

4. The length of the handle 73 is preferably such that the displacement of the sample from the tube 31 (as above described) automatically re-positions the surface 43 of the temperature-determining unit 29 proximate to the reduced end of the transitional portion 55 of the sample tube 31 (as described above, under ASSEMBLY OF PREPARATION APPARATUS, Step 3).

The temperature-determining unit 29 described more fully in the above-referenced application functions in combination with the above-mentioned meat-sample analyzer 101. Upon loading of the ground-meat sample 79 into the sample tube 31, the temperature probe 39 becomes substantially embedded within the meat sample (see FIG. 2). After a predetermined period of time, the current-to-frequency converter 50 (FIG. 11), connected to the temperature probe 39, begins to generate an information signal relatable to the temperature of the meat sample within the sample tube 31. The above-discussed analyzer 101 uses the meat-sample temperature information in calculating the relative lean or fat content of the meat sample in the sample tube 31.

What has been illustrated and described herein is a novel method and apparatus for preparing a ground-meat sample for relative fat or lean compositional analysis. While the preparation apparatus of the instant invention has been illustrated and described with reference to a preferred embodiment, the invention is not limited thereto. On the contrary, alternatives, changes or modifications may become apparent to those skilled in the art upon reading the foregoing description. Accordingly, such alternatives, changes or modifications are to be considered as forming a part of the invention insofar as they fall within the spirit and scope of the appended claims.

We claim:

1. A method for preparing an analyzable meat sample for compositional analysis comprising: (1) obtaining a predetermined quantity of ground meat, said meat having a predetermined particle size; (2) forming said meat into a layer having a predetermined thickness; (3) isolating a first portion of said layer from the remainder; (4) urging said first portion into an elongate hollow member having an axis, an open end, and a resistive end movable along said axis relative to said open end; (5) urging said first portion and said resistive end together so as to produce a substantially air void-free isolate out of said first portion; (6) isolating a subsequent portion of said layer from the remainder and urging said subsequent portion into said hollow member and against said isolate already in said hollow member thereby adding to said isolate already in said hollow member and causing said resistive end and said isolate engaging said resistive end to move axially through said member for filling said member; (7) repeating step (6) until said member is predeterminedly filled with said meat thereby producing said analyzable meat sample.

2. A method for preparing a sample of meat for compositional analysis comprising the steps of: spreading a layer of ground meat upon a surface; isolating a first portion of the meat spread upon said surface, and packing said isolated first portion into an open end of an elongate tubular container so as to substantially eliminate any air voids in said first portion, once packed into said container; repeating said isolating and packing until said container is packed with a quantity of said meat, substantially free of air voids; transferring said predetermined quantity of meat from said first container into a second container for analysis while substantially maintaining said absence of air voids therein.

3. A method in accordance with claim 2 wherein the step of transferring further includes the step of aligning said open end of said first container with an open end of said second container, and thereafter urging said meat from said first container into said second container.

4. A method in accordance with claim 2 and further including, following said spreading, the step of mixing said ground meat so as to obtain a substantially uniform temperature throughout said predetermined quantity thereof.

5. A method in accordance with claim 2, wherein the step of spreading further includes distributing said meat to a substantially uniform depth across said surface.

6. A method in accordance with claim 2 wherein the step of packing further includes the step of impinging upon the isolated and packed section of meat within said first container so as to retain it tightly packed within said first container substantially free of air voids.

7. A method according to claim 2 and further including, following the filling of said first container with a predetermined quantity of meat, the further step of gathering any fibers of said meat extending outwardly from the open end of said first container and the step of urging said fibers against the meat in said filled container.

8. Apparatus for loading a ground meat sample into an elongate hollow container insertable in a test apparatus, comprising: means defining an axially movable end closure for said container; and means for axially urging said ground meat into said container so as to axially move said end closure means to substantially prevent the formation of air voids in the ground meat within said container; said end closure means and said urging means first acting as a unit separated from said elongate hollow container to collect the ground meat from a source thereof, the ground meat collected therewith being the immediate source of the ground meat sample loaded into said elongate hollow container; and wherein said end closure means includes sealing means slidably engageable with an inner surface of said container to assure substantially uniform loading of said sample into said container while further aiding in prevention of air void formation.

9. Apparatus in accordance with claim 8 wherein said movable closure means comprises a temperature determining unit dimensioned to slidably fit within said container; and further including an elastomeric sealing element engageable about an outer periphery of said temperature determining unit to form a slidably movable seal with the inner surface of said container.

10. Apparatus in accordance with claim 8 wherein said urging means comprises an elongate hollow loading vessel, and a plunger axially movable within said loading vessel.

11. Apparatus for loading a ground meat sample into an elongate hollow container insertable in a test apparatus, comprising: means defining an axially movable end closure for said container; and means for axially urging said ground meat into said container so as to axially move said end closure means to substantially prevent the formation of air voids in the ground meat within said container; said end closure means and said urging means first acting as a unit separated from said elongate hollow container to collect the ground meat from a source thereof, the ground meat collected therewith being the immediate source of the ground meat sample loaded into said elongate hollow container; wherein said movable closure means comprises a member dimensioned to slidably fit within said container; and further including an elastomeric sealing element engageable about an outer periphery of said member to form a slidably movable seal with the inner surface of said container.

12. An apparatus for preparing a ground-meat sample for compositional analysis, said apparatus comprising: a temperature-determining unit; a substantially hollow, open-ended sample container defining a longitudinal axis, said temperature-determining unit being insertable into said sample container and axially slidable therein for closing an open end thereof; a substantially hollow loading vessel defining a longitudinal axis and having at least one open end; a plunger insertable into said loading vessel and axially movable therein, said loading vessel being axially alignable with said sample container and said plunger being axially slidable therein; and a loading base having a substantially hollow, outwardly-extending member, said sample container being insertable into said hollow member, said ground-meat sample when loaded in said loading vessel being transferable from said loading vessel into said sample container by a predetermined force imposed axially upon said plunger.

13. The apparatus of claim 12, wherein said temperature-determining unit and said sample container are cylindrical, the outer diameter of said unit being relatively less than the inner diameter of said container.

14. The apparatus of claim 12, wherein said loading vessel is cylindrical; and wherein said plunger comprises a disc having an outer diameter relatively less than the inner diameter of said loading vessel, and a handle affixed to and extending substantially perpendicularly from said disc.

15. The apparatus of claim 12, wherein said loading vessel includes an end closure, said end closure including a substantially centrally located through aperture for slidably receiving said handle.

16. The apparatus of claim 15, wherein said handle and said aperture are cylindrical, the external diameter of said handle being relatively less than the inner diameter of said aperture.

17. The apparatus of claim 12, wherein a portion of the inner surface of said sample container converges radially and wherein the outer periphery of said loading vessel converges to interfit with said portion of the inner surface of said sample container.

18. The apparatus of claim 12, wherein said loading base hollow member and said sample container are cylindrical, the inner diameter of said loading base hollow member being relatively greater than the outer diameter of said sample container.

19. The apparatus of claim 12, wherein said temperature-determining unit includes a circumferential groove; and further including an elastically deformable O-ring, for sealingly engaging said groove and projecting radially outwardly of said temperature-determining unit for sealing, slidable engagement with the inner surface of said sample container.

20. An apparatus for analyzing a sample of ground meat and the like comprising: a substantially hollow open-ended sample container defining a longitudinal axis; a temperature-determiing unit removably insertable into said sample container and axially slidable therein for closing an open end thereof and sensing the temperature of a sample packed into said container, said container being removably insertable into means for sensing and analyzing its constituents.

21. The apparatus of claim 20, wherein said temperature-determining unit and said sample container are cylindrical, the outer diameter of said unit being relatively less than the inner diameter of said container.

22. The apparatus of claim 21, wherein said temperature-determining unit includes annular means for wiping an internal surface of said container as the unit slides axially of the container.

* * * * *